United States Patent
DeFonzo

(12) 
(10) Patent No.: US 6,193,651 B1
(45) Date of Patent: Feb. 27, 2001

(54) SURGICAL RETRACTOR

(75) Inventor: Stephan A. DeFonzo, Bridgeport, CT (US)

(73) Assignee: United States Surgical Corporation, Norwalk, CT (US)

( * ) Notice: Subject to any disclaimer, the term of this patent is extended or adjusted under 35 U.S.C. 154(b) by 0 days.

(21) Appl. No.: 08/806,469

(22) Filed: Feb. 26, 1997

Related U.S. Application Data

(63) Continuation-in-part of application No. 08/546,008, filed on Oct. 20, 1995.

(51) Int. Cl.[7] .................................................. A61B 1/22
(52) U.S. Cl. ........................ 600/201; 600/210; 600/213; 600/226
(58) Field of Search .................................. 600/201, 210, 600/213, 214, 215, 226, 231, 235, 217, 225, 248, 227, 232, 233, 245, 181

(56) References Cited

U.S. PATENT DOCUMENTS

| | | | |
|---|---|---|---|
| Re. 34,150 | * 12/1992 | Santilli et al. | ............................ 128/20 |
| 1,400,616 | * 12/1921 | McCroryt et al. | ............... 600/234 X |
| 2,186,143 | * 1/1940 | Neugass | ............................ 600/245 X |
| 2,383,705 | 8/1945 | Bortagaray . | |
| 2,473,266 | 6/1949 | Wexler . | |
| 2,693,795 | 11/1954 | Grieshaber . | |
| 2,751,902 | 6/1956 | Loeffler . | |
| 3,070,088 | 12/1962 | Brahos . | |
| 3,227,156 | 1/1966 | Gauthier . | |
| 3,384,078 | 5/1968 | Gauthier . | |
| 3,467,079 | 9/1969 | James . | |
| 3,509,873 | 5/1970 | Karlin et al. . | |
| 3,522,799 | 8/1970 | Gauthier . | |
| 3,680,546 | 8/1972 | Asrican . | |
| 3,724,449 | 4/1973 | Gauthier . | |
| 3,747,592 | 7/1973 | Santos . | |
| 3,749,088 | 7/1973 | Kohlmann . | |
| 3,965,890 | 6/1976 | Gauthier . | |
| 4,010,741 | 3/1977 | Gauthier . | |
| 4,156,424 | 5/1979 | Burgin . | |
| 4,165,746 | 8/1979 | Burgin . | |
| 4,263,899 | 4/1981 | Burgin . | |
| 4,421,107 | 12/1983 | Estes et al. . | |
| 4,566,448 | 1/1986 | Rohr, Jr. . | |
| 4,616,635 | 10/1986 | Caspar et al. . | |
| 4,622,955 | 11/1986 | Fakhrai . | |
| 4,627,421 | 12/1986 | Symbas et al. . | |
| 4,726,356 | 2/1988 | Santilli et al. . | |
| 4,747,394 | 5/1988 | Watanabe . | |
| 4,747,395 | 5/1988 | Brief . | |
| 4,754,746 | 7/1988 | Cox . | |
| 4,765,311 | 8/1988 | Kulik et al. . | |

(List continued on next page.)

FOREIGN PATENT DOCUMENTS

| | | |
|---|---|---|
| 2302078 | 9/1976 | (DE) . |
| 116547 | 6/1918 | (GB) . |
| 2082459 | 8/1981 | (GB) . |

Primary Examiner—Beverly M. Flanagan

(57) ABSTRACT

A surgical retractor comprising a base adapted to lie on the patient's skin, a handle slidably mounted with respect to the base, a tissue retracting blade extending from the handle, and a locking member movable from at least a first position to a second position to retain the tissue retracting blade in a selected position. A light guide illuminates the surgical site during use. An angle adapter can be mounted to the base to increase the angle of the tissue retracting blade with respect to the tissue. A method for accessing the saphenous vein to facilitate harvesting the vein is also disclosed comprising the steps of making a small incision in the leg of a patient, positioning a retractor on a patient's leg such that a retractor blade extends into the incision and a base lies on the surface of the patient's leg and pulling the retractor blade away from the patient to lift the tissue away from the underlying saphenous vein.

19 Claims, 17 Drawing Sheets

U.S. PATENT DOCUMENTS

| | | |
|---|---|---|
| 4,793,346 | 12/1988 | Mindich . |
| 4,813,401 | 3/1989 | Grieshaber . |
| 4,829,985 | 5/1989 | Couetil . |
| 4,852,552 | 8/1989 | Chaux . |
| 4,865,019 | 9/1989 | Phillips . |
| 4,924,857 | 5/1990 | Mahmoodian . |
| 4,949,707 | 8/1990 | LeVahn et al. . |
| 5,025,779 | 6/1991 | Bugge . |
| 5,035,232 * | 7/1991 | Lutze et al. .................... 600/226 X |
| 5,052,373 | 10/1991 | Michelson . |
| 5,052,374 | 10/1991 | Alvarez-Jacinto . |
| 5,067,477 | 11/1991 | Santangelo . |
| 5,231,974 | 8/1993 | Giglio et al. . |
| 5,299,563 | 4/1994 | Seton . |
| 5,373,840 | 12/1994 | Knighton . |
| 5,400,774 | 3/1995 | Villalta et al. . |

* cited by examiner

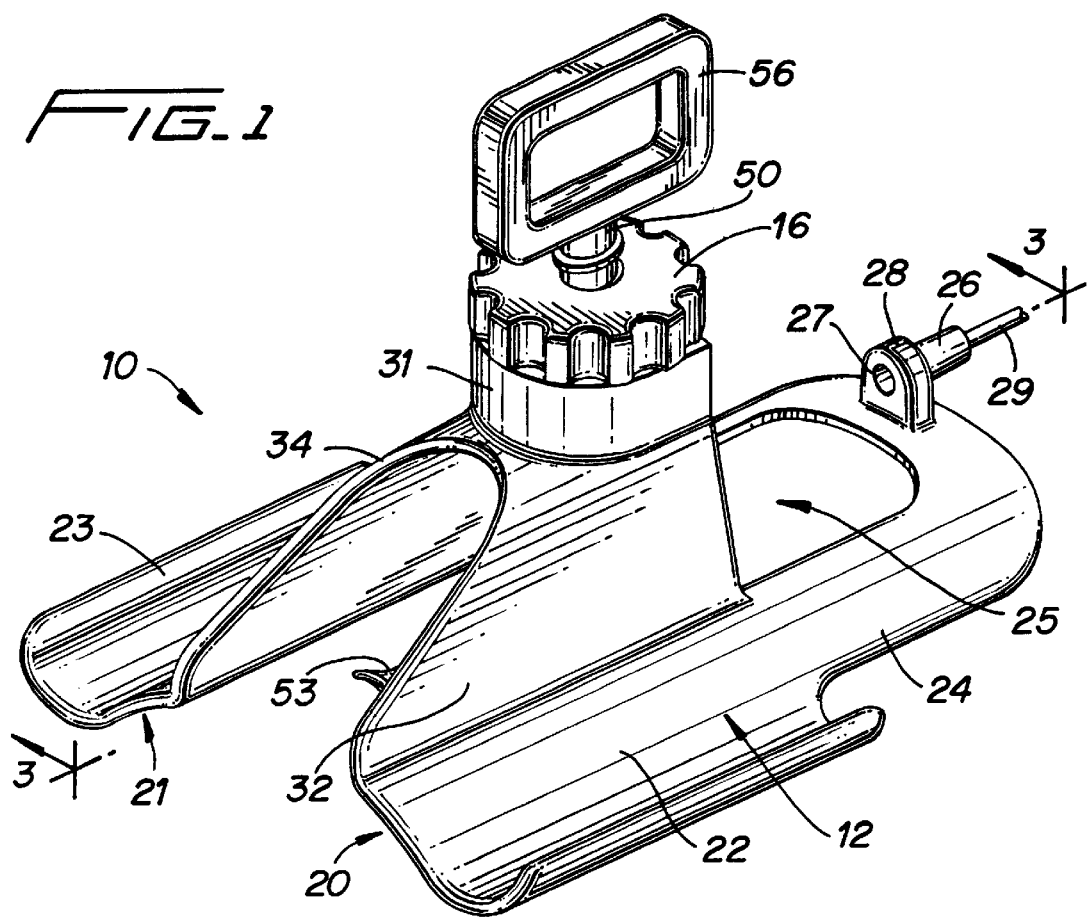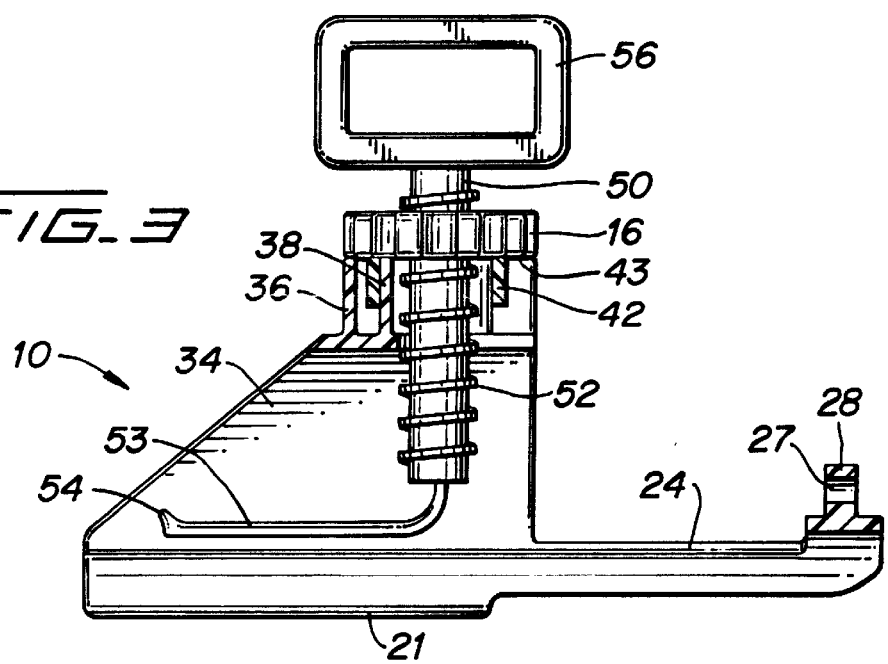

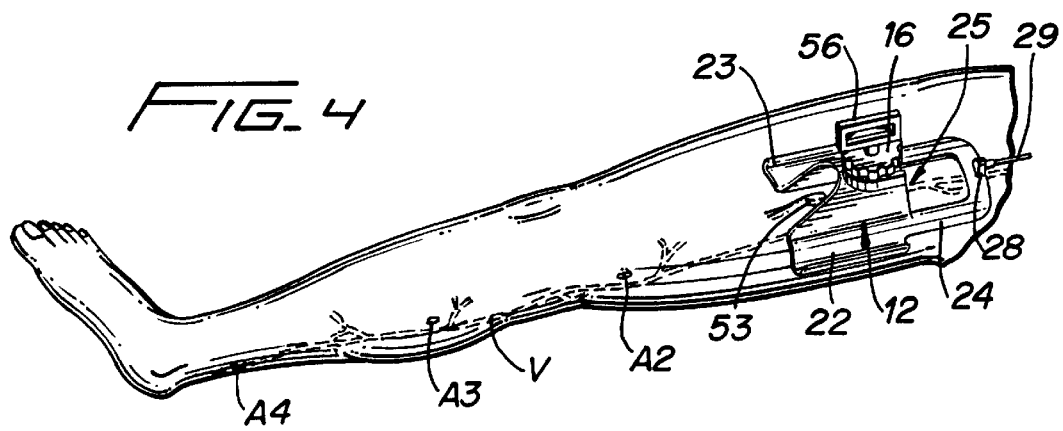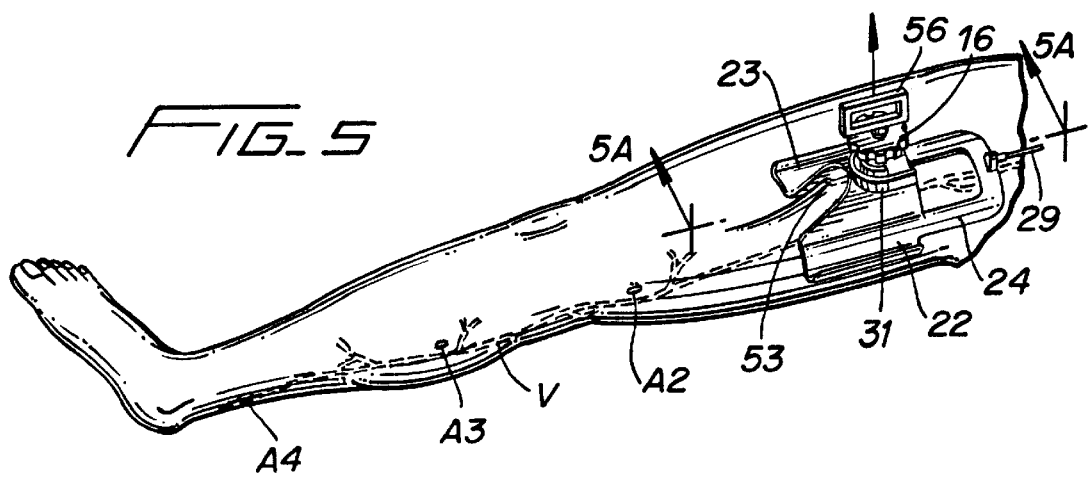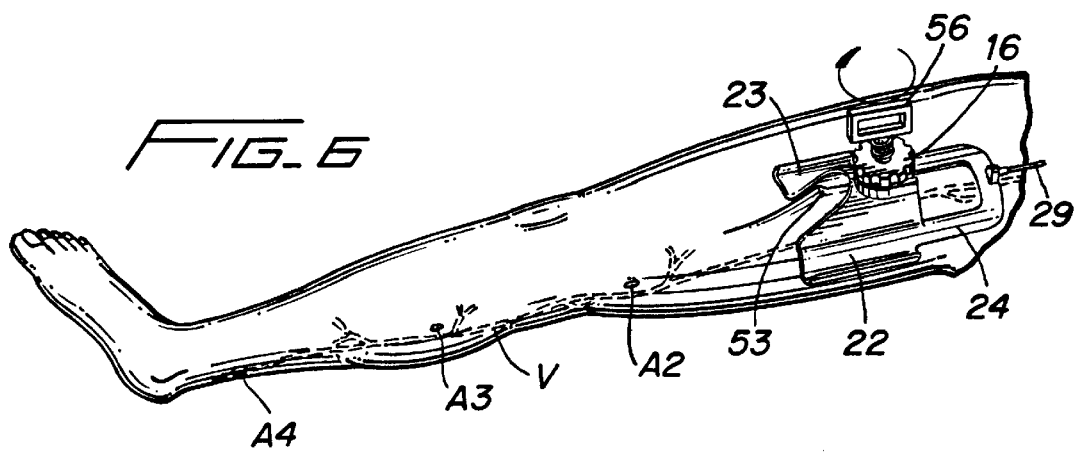

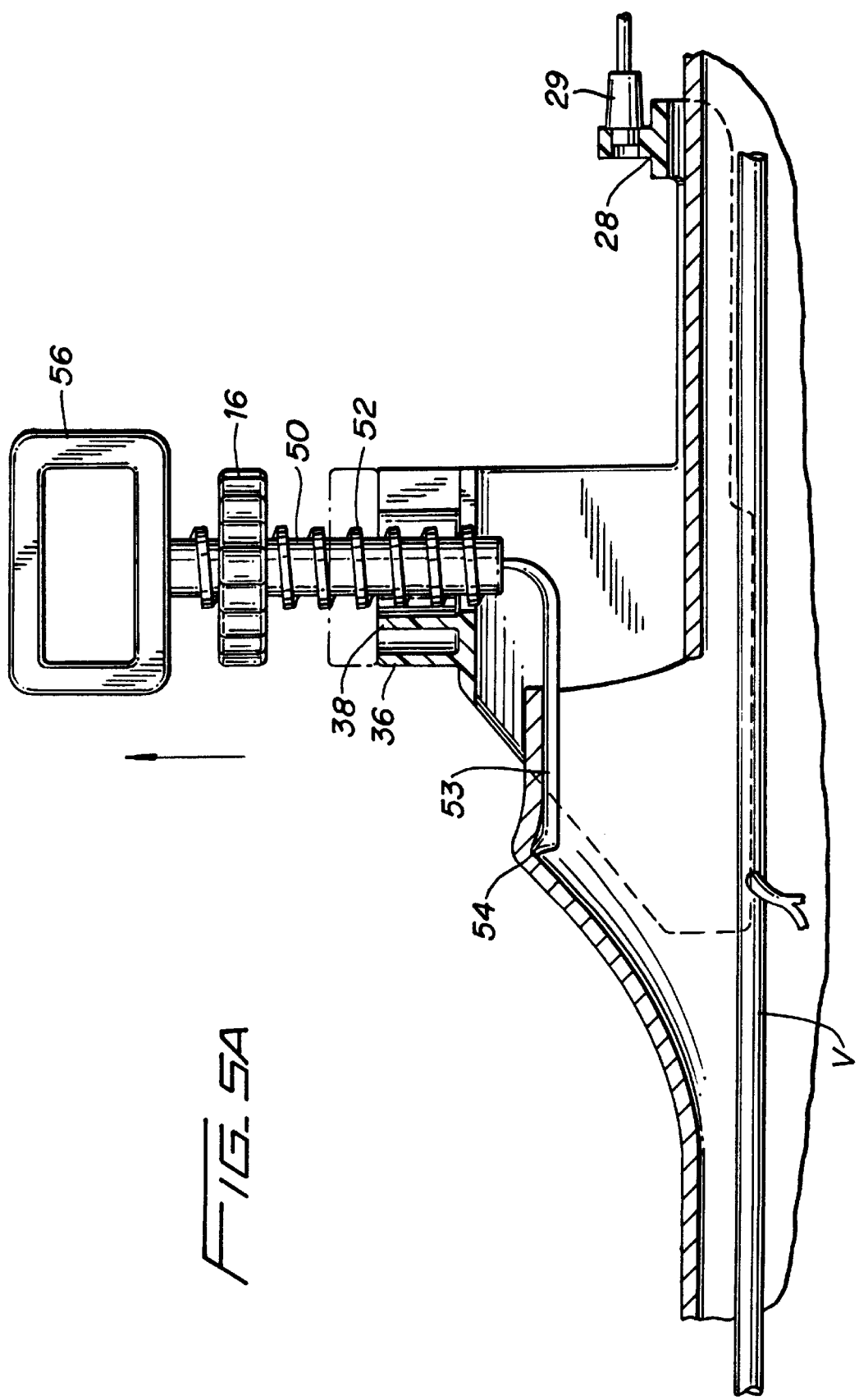

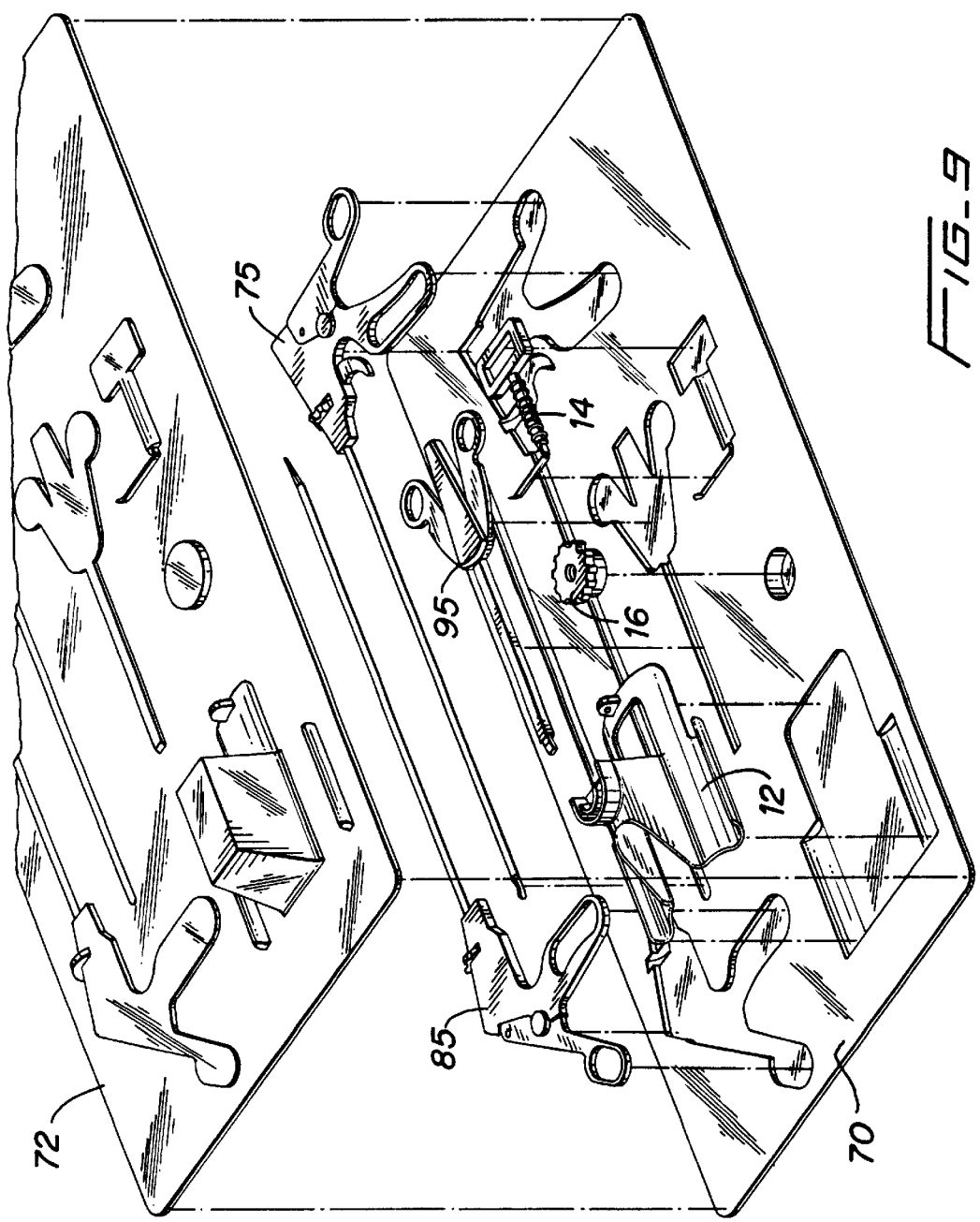

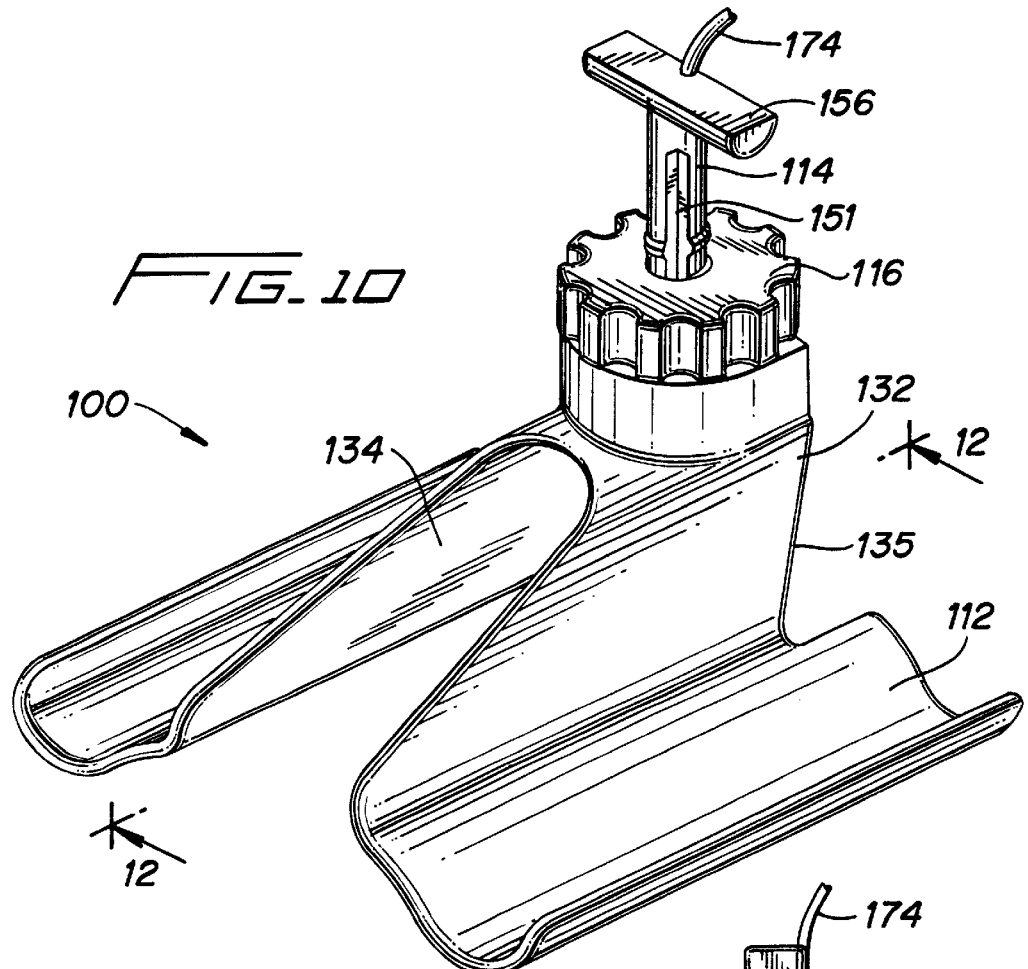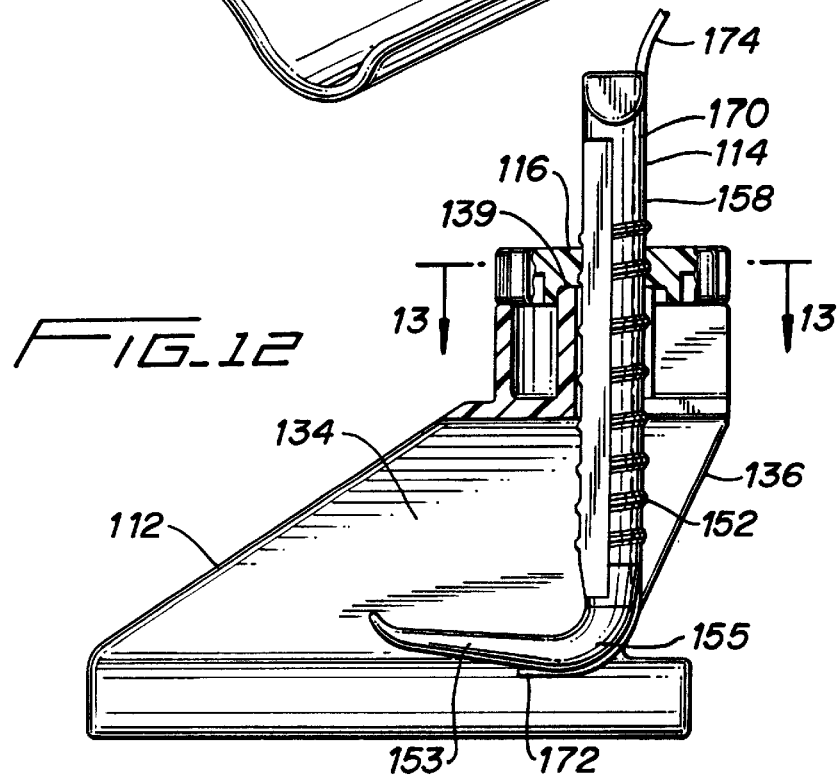

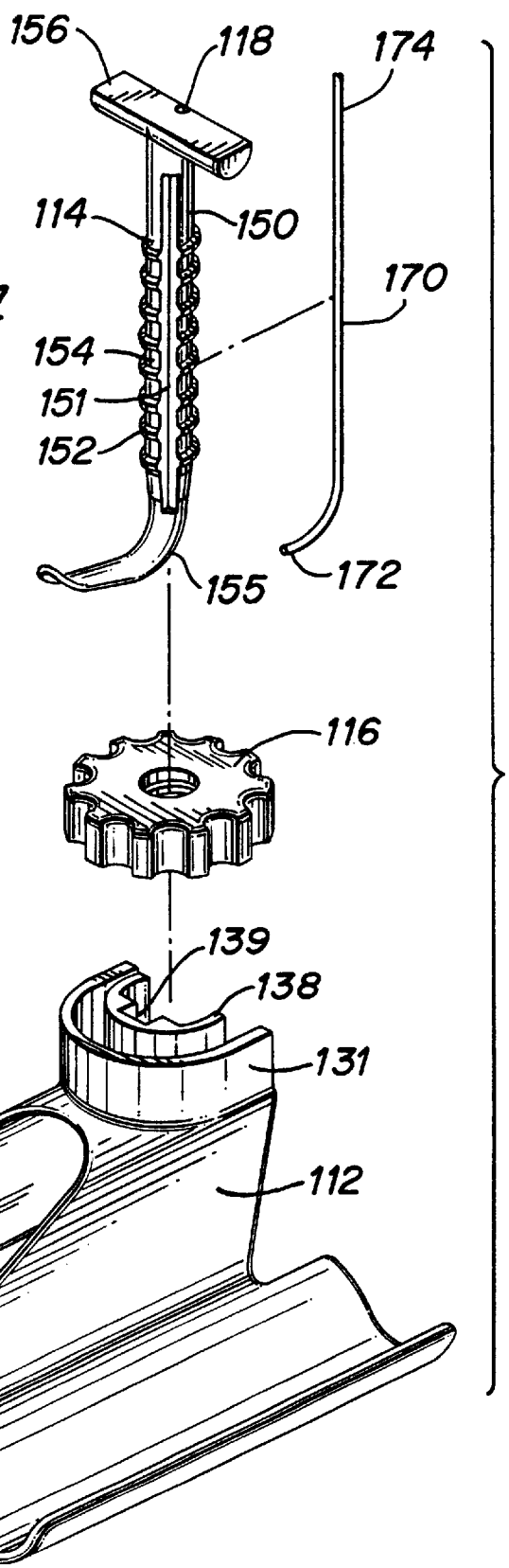

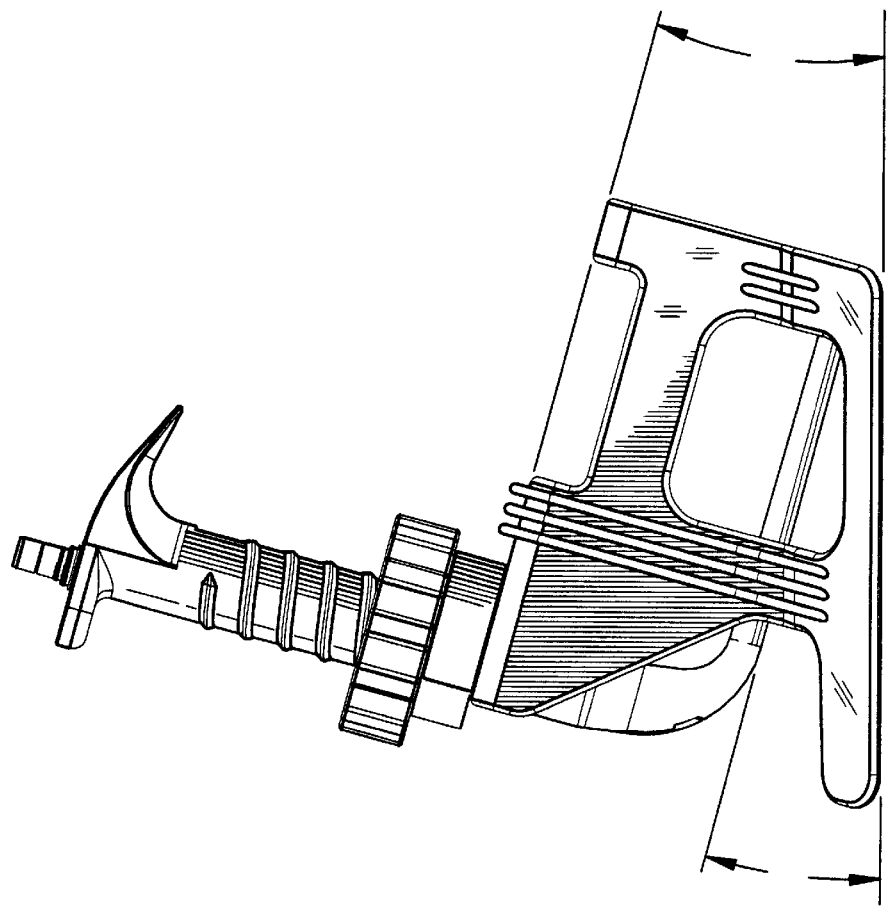
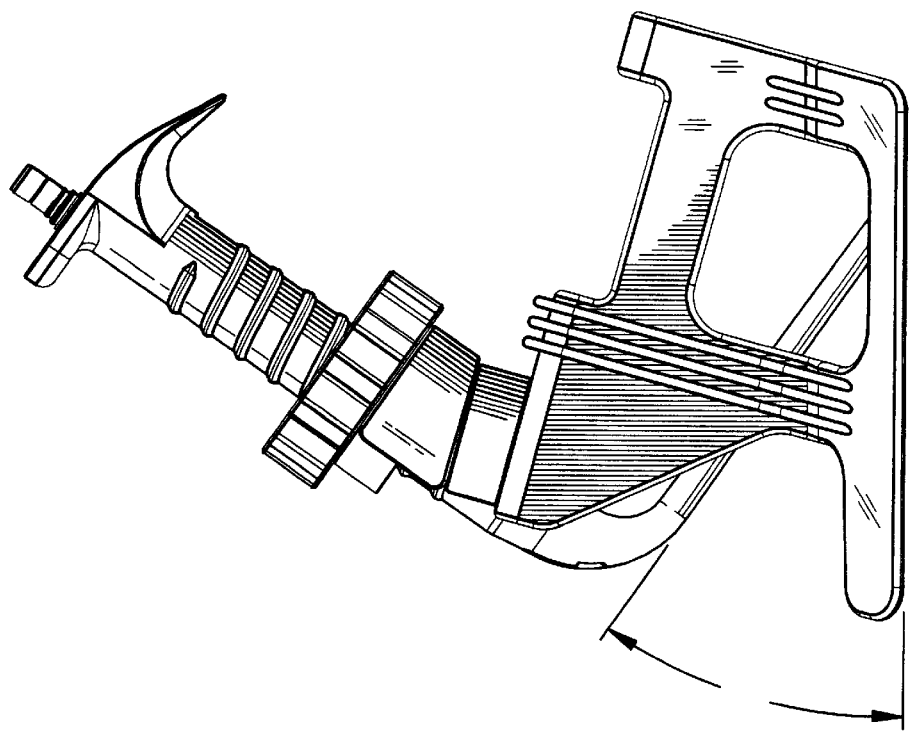
FIG. 18B
FIG. 18A

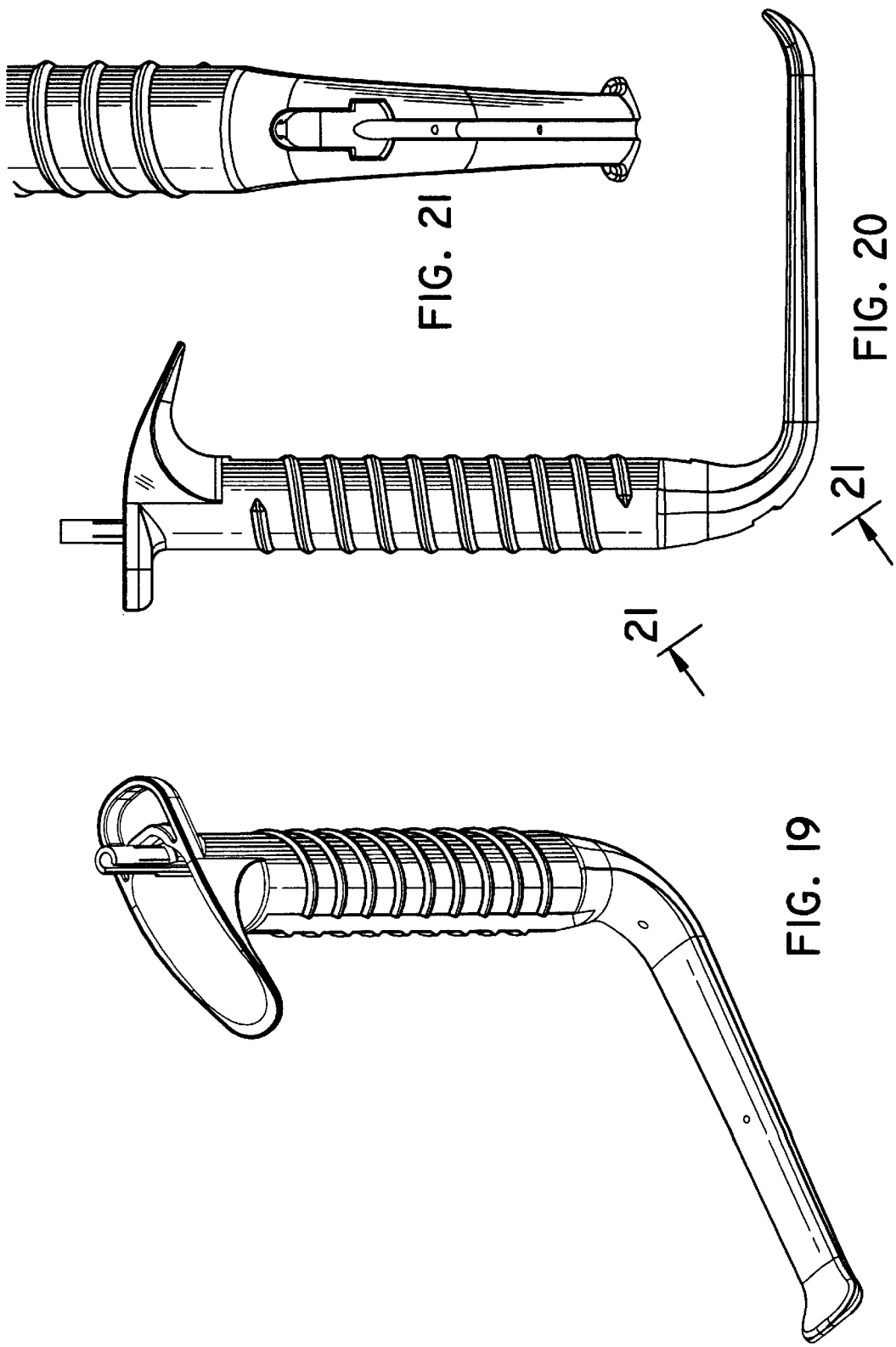

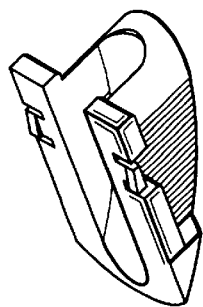
FIG. 23
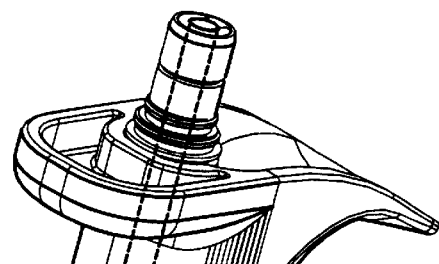
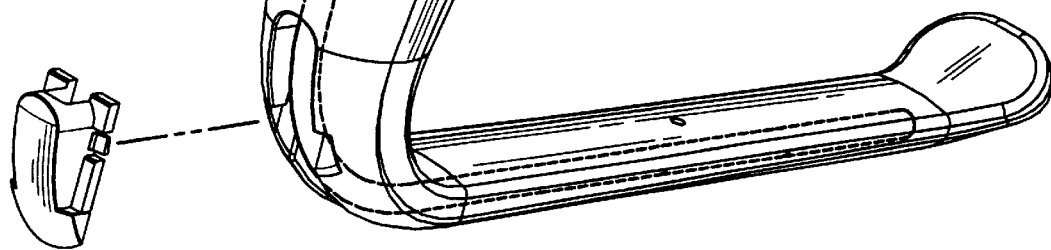
FIG. 24 ns
SURGICAL RETRACTOR

This application is a continuation-in-part of U.S. application Ser. No. 08/546,008, filed Oct. 20, 1995, the contents of which are incorporated herein by reference.

BACKGROUND

1. Technical Field

This application relates to a surgical retractor, and more particularly, to a surgical retractor which facilitates the harvesting of veins.

2. Background of the Related Art

In certain surgical procedures, it is necessary to remove an artery or vein from the patient. For example, in coronary artery bypass surgery (CABG), to re-route the blood flow to or from the heart to bypass a blockage in the coronary artery, an artery or vein is harvested from the patient and connected to the coronary artery to enable the unobstructed flow of blood.

In certain instances, e.g. when only a short graft is required, the mammary artery can be harvested and used for CABG. However, the mammary artery is oftentimes of insufficient length. Therefore, the patient's saphenous vein is most often utilized. The saphenous vein runs the length of the leg and is about ¼ to 1 inch below the skin. The most common method of removing the saphenous vein currently performed by surgeons involves making an incision in the patient's leg extending the length of the section of the vein to be removed. Frequently, this requires an incision running the entire length of the leg, from the ankle to the groin, which can be over 40 inches in length. Once the leg is opened in this manner, the surgeon, utilizing a light source supported on headgear or a headband, dissects the vein from the surrounding tissue and ligates and severs the vein from its numerous branches along its length. The vein is then cut at both ends and removed from the patient for use as a graft attached to the coronary artery or aorta. After removal of the vein, the leg incision is sutured.

Such formation of a large leg incision has many disadvantages. It is time consuming, complicates the procedure, creates a large scar, and increases the risk of infection and skin necrosis. It also adds to the expense of the procedure by requiring additional surgeon time to close the leg incision. Moreover, it increases the patient's discomfort and prolongs the patient's recovery time. In fact, the recovery time from the leg incision can take even longer than the recovery time from the chest incision from the heart surgery.

The need for a less invasive method and instrumentation to remove the saphenous vein is recognized in the field. For example, in U.K. Patent No. 2,082,459, an apparatus is disclosed for harvesting the saphenous vein utilizing two small incisions. A center rod is inserted into the lumen of the vein, and the tubular body having a series cutting blades is introduced over the center rod and passed along the vein to cut the tributaries and fatty tissue around the vein. U.S. Pat. No. 4,793,346 to Mindlich discloses an apparatus which has a pair of knife blades extending from an elongate plastic tube. The tube has an inner diameter larger than the outer diameter of the vein. In use, the tube is inserted through an incision, and guided over the vein by a flexible guide which is inserted through the vein. The tube is rotated as it is advanced so that the knife blades can sever the vein branches. Electrically conductive wires are coupled to the knife blades to cauterize the severed end of the branches. U.S. Pat. No. 5,373,840 to Knighton discloses an endoscope and method for vein removal under visualization. A dissecting tool is inserted through one of the endoscope channels to separate the blood vessel from the connective tissue and a forceps is inserted through a second channel to hold the vessel during the procedure. The endoscope is inserted through a small incision and the dissecting tool is advanced along the vein. When a side branch is encountered, the dissection tool is removed and a ligating-cutting tool is inserted through the channel to sever the side branch.

Each of the instruments of the prior art described above are complex and expensive. Furthermore, they require the procedure to be performed in a tight working space as the vein is not separated from the surrounding tissue and the instruments are wedged between the vein and the tissue.

It would be advantageous to provide an apparatus which could minimally invasively separate the skin (and subcutaneous tissue) from the vein to enable dissecting and ligating instrumentation to be inserted through small incisions to facilitate removal of the saphenous vein. It would also be advantageous to equip such apparatus with illumination capabilities to enable the surgeon to better visualize the vein as it is dissected. This would not only eliminate the need for the surgeon to wear cumbersome head gear, but would avoid the expense involved with the use of an endoscope as well as avoid the additional time required for the constant withdrawal and reinsertion of the instruments through the endoscope's working channels.

SUMMARY

The present application discloses a retractor which advantageously increases the working space to facilitate minimally invasive harvesting of the vein from the patient. More specifically, the retractor lifts the skin and subcutaneous tissue away from the saphenous vein to improve visibility and enable dissecting and ligating instruments to more easily access the vein.

The retractor has a base adapted to lie on the patient's skin and a tissue retracting blade movably mountable to the base. Preferably the retracting blade extends from a handle which is slidably mounted with respect to the base. A locking member cooperating with the handle and movable to retain the tissue retracting blade in a selected position can be provided. The locking member preferably comprises a rotatable knob which engages threads on a shaft portion of the handle. The apparatus preferably includes means in the form of a light guide for enabling illumination of the surgical site. Optionally, a light shield is provided to shield a portion of the light emanating from the light guide. The apparatus may also include an adapter mounted to the base to increase the angle of the tissue retracting blade with respect to the tissue.

The base preferably has a pair of spaced apart legs adapted to lie on the patient's skin and an upper portion having a support to receive the tissue retracting member wherein the upper portion of the base is angled such that its front portion is raised with respect to its back portion.

A method for accessing the saphenous vein to facilitate harvesting the vein is also disclosed comprising the steps of making a small incision in the leg of the patient, positioning a retractor on the patient's leg such that a retractor blade extends into the incision and a base portion lies on the surface of the patient's leg, and pulling the retractor blade away from the patient to lift the tissue away from the underlying saphenous vein.

BRIEF DESCRIPTION OF THE DRAWINGS

Various embodiments are described herein with reference to the drawings, wherein FIG. 1 is a perspective view of a first embodiment of the surgical retractor;

FIG. 3 is a cross-sectional view taken along lines 3—3 of FIG. 1 showing the handle and retractor blade in the initial position;

FIG. 4 is a perspective view showing the surgical retractor positioned in a first incision in the patient's left leg and the retractor handle in the initial position;

FIG. 5 is a perspective view similar to FIG. 4 showing the handle and retractor blade in the deployed position to separate the skin and subcutaneous tissue from the vein;

FIG. 5A is a cross-sectional view taken along lines 5A—5A of FIG. 5 showing the handle and retractor blade in the deployed position;

FIG. 6 is a perspective view similar to FIG. 5 showing rotation of the locking knob into the locking position to retain the handle and retractor blade in the selected position;

FIG. 9 is a perspective view of a surgical kit for harvesting the saphenous vein which includes the surgical retractor of FIG. 1;

FIG. 10 is a perspective view of a second embodiment of the surgical retractor;

FIG. 11 is an exploded perspective view of the retractor of FIG. 10;

FIG. 12 is a cross-sectional view of the surgical retractor taken along lines 12—12 of FIG. 10 showing the handle and retractor blade in the initial position;

FIG. 13 is a cross-sectional view taken along lines 13—13 of FIG. 12 showing the keyway for orienting the handle with respect to the base of the retractor.

FIG. 18A is a side view of the retractor blade mounted on the base with the use of the angle adapter;

FIG. 18B is a side view of the retractor blade mounted on the base without the use of the angle adapter;

FIG. 19 is a perspective view of the retractor blade of FIG. 14 prior to insertion of the light guide;

FIG. 20 is a side view of the retractor blade of FIG. 19;

FIG. 21 is a view taken along lines 21—21 of FIG. 20;

FIG. 23 is an enlarged perspective view of the light shield;

FIG. 24 illustrates the attachment of the light shield to the retractor blade;

DETAILED DESCRIPTION OF PREFERRED EMBODIMENTS

Figure 2:
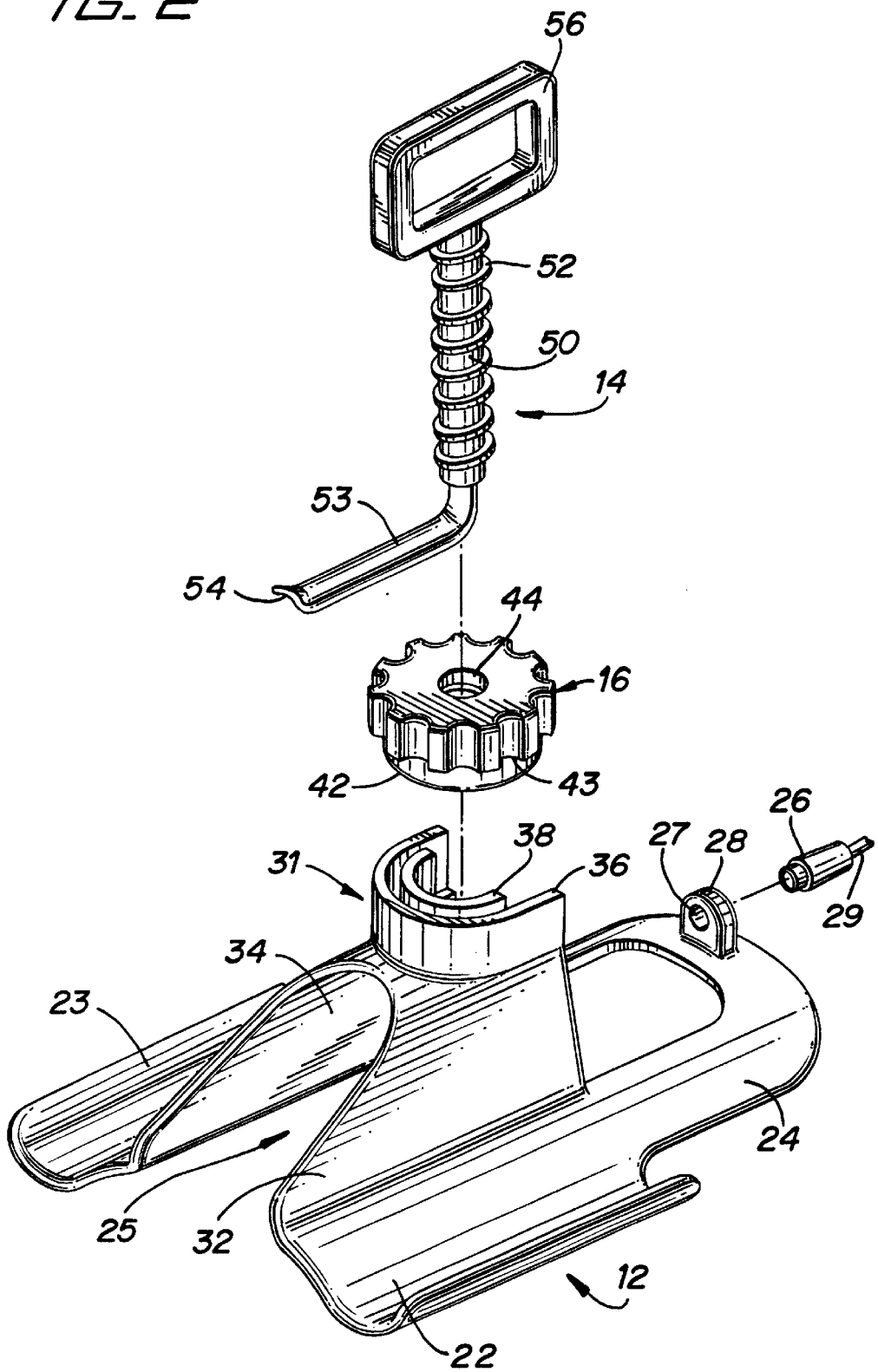
FIG. 2 is an exploded perspective view of the retractor of FIG. 1.
Figure 7:
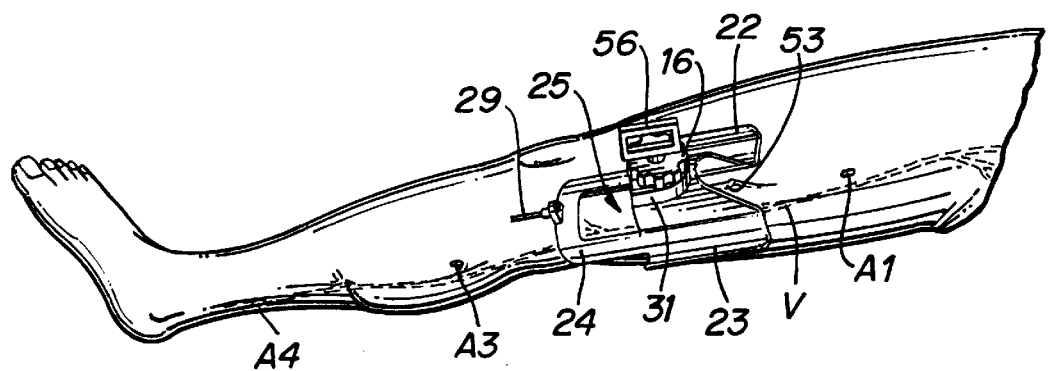
FIG. 7 is a perspective view illustrating the surgical retractor positioned in a second incision, oriented in the opposite direction of that of FIG. 4 and showing the handle and retractor blade in the initial position.

Referring now to the drawings wherein like reference numerals identify similar or identical parts throughout the views, and particularly to FIGS. 1–3, the surgical retractor of the present application is identified generally by reference numeral 10. Retractor 10 includes a handle 14 having a hook portion or retractor blade 53 for engaging the tissue to be retracted, a base 12 for supporting handle 14, and a locking knob 16 for retaining the handle 14 and retractor blade 53 in the selected position.

In short, the retractor blade 53 is placed inside a skin incision and is manually pulled upwardly by pulling on handle 14 to lift the tissue layers. This separates the lifted tissue from the underlying structure to improve access for performing the surgical procedure as described below.

Base 12 of retractor 10 has a pair of spaced apart legs 22, 23, extending from walls 32, 34, respectively, which curve upwardly and outwardly away from the center of the base 12. The skin engaging bottom surfaces 20, 21 of legs 22,23, respectively, are adapted to lie on the patient's skin. Walls 32, 34 are spaced apart to form gap 25 to allow access to the surgical site with the necessary instrumentation.

Extension 24 has a support 28 with an aperture 27 formed therein configured to receive a conventional adapter 26 for mounting an optical fiber 29 to illuminate the surgical site. Alternatively, a light pipe can be provided to guide light from a conventional light source such as Storz Coldlight Fountain. Thus, the optical fiber or light pipe provides a means for enabling illumination of one surgical site as an alternative to the headgear currently worn by surgeons. It should be understood that the means for enabling illumination could alternately be positioned at other locations with respect to the base and the handle as long as it performs the desired function.

Walls 32, 34, as shown, extend downwardly and outwardly from neck portion 31 and are integrally formed with the respective leg 22, 23. A U-shaped outer wall 36 and a U-shaped inner wall 38 are formed on neck portion 31 and are configured to receive the locking knob 16 as best seen in FIG. 2. The opening in the U-shaped walls 36, 38 allows the handle 14 to be mounted to the base 12.

Handle 14 is slidably mounted with respect to base 12 and has a shaft 50 dimensioned for slidable reception in the opening in inner wall 38. Shaft 50 has an integral retractor blade 53 extending substantially perpendicular thereto, terminating in atraumatic tip 54. Although shown as integral, it is also contemplated that the retractor blade can be a separate element attached to shaft 50. A plurality of external threads 52 are formed along the length of shaft 50 to engage the internal threads on locking knob 16 as will be described below. Handle grip 56 is illustrated with an opening for the user's fingers to facilitate grasping. It should be appreciated that alternate grips can be utilized.

With continued reference to FIGS. 1–3, locking knob 16 has an axial opening 44 to receive shaft 50 of handle 14 and internal threads which engage the external threads 52 of handle 14. Cylindrical flange 42 is seated in the space between the inner and outer walls 38, 36 and bottom surface 43 rests on the upper surface of inner and outer walls 38, 36 when the locking knob 16 is in the locking position.

In use, retractor portion (blade) 53 is inserted through an incision formed in the patient and the base 12 is placed on the patient's skin. Handle grip 56 is grasped by the user and the handle 14 is pulled upwardly away from the patient. This causes the blade 53 to lift the patient's skin and a portion of the subcutaneous tissue. When the handle 14, i.e. the retractor blade 53, is in the desired position, locking knob 16 is rotated clockwise to slide it towards base 12 until flange 42 is seated in the space between the outer and inner walls 36, 38, and lower surface 43 rests on walls 36, 38, thereby locking handle 14 in position. This frees the surgeon's hands as it effectively retains the tissue in the lifted position without the surgeon having to hold the handle 14. When the surgeon desires to release the retractor blade 53, locking knob 16 is rotated counterclockwise, thereby releasing the locking engagement of locking knob 16 and shaft 50 to allow the handle 14 to be lowered to return the tissue to the initial portion. The retractor blade 53 can then be removed from the incision.

It should be noted that if controlled progressive lifting of the retractor blade 53 is desired, initially the locking knob 16 can be placed in the lowermost position, i.e. flange 42 positioned between U-shaped walls 36,38 and lower surface 43 resting atop walls 38, 36. Rotation of knob 16 clockwise will then progressively move retractor blade 53 upwardly to lift the skin.

By way of example, the retractor of the present invention will be described in conjunction with saphenous vein harvesting as illustrated in FIGS. 4–8, although other uses of the retractor are possible. The retractor 10 advantageously enables the saphenous vein V to be harvested by requiring only several (e.g. four), small incisions in the leg, each about 40 mm, as contrasted with a longitudinal incision running the length of the leg. As shown, four incisions A1, A2, A3 and A4 are made in the leg, two above the knee and two below the knee. The retractor 10 is inserted into each incision to separate the surrounding tissue from the vein to improve access to the vein and increase the working space. More specifically, it lifts the tissue away from the vein to enable the vein to be dissected and ligated along the extent of its length which is accessible by the surgical instruments inserted through the incision. The retractor 10 is inserted in each incision in two directions (e.g. FIG. 4 and FIG. 7) so the vein can be accessed in both directions through each incision.

More particularly, as shown in FIG. 4, the retractor blade 53 of retractor 10 is placed through incision A1 in the leg with the engaging surfaces of legs 22, 23 of the base 12 resting on the patient's skin. Optical fiber 29 illuminates the surgical site. Handle grip 56 is pulled upwardly in the direction of the arrow of FIG. 5 to lift retractor blade 53, thereby lifting the skin and a portion of the subcutaneous tissue away from the saphenous vein V (see also FIG. 5A). When the skin and subcutaneous tissue have been lifted to a desired degree to provide a sufficient gap for visualization and access to the branches of the vein, locking knob 16 is rotated clockwise as shown in FIG. 6 to abut inner and outer walls 38, 36 to secure the handle shaft 50 in position. This locks the retractor blade 53 in position so the surgeon can release the handle 14 and free his hands for the procedure, with the blade 53 maintaining the working gap between the tissue and the vein.

If more controlled progressive lifting of the tissue is desired as described above, the locking knob 14 can initially be seated on the upper surface of inner and outer walls 38, 36 and rotated clockwise to progressively lift the retractor blade 53.

Once the tissue is lifted, a dissecting and ligating instrument are inserted through the gap 25 in the base 12 to ligate and dissect the branches from the vein. As illustrated, this dissects and ligates the branches to the left of the incision as viewed in FIG. 4. On example of instruments which can be used are the Auto Suture ENDO SHEARS* instrument and Auto Suture PREMIUM SURGICLIP* clip applied asterisk denotes trademark of United States Surgical Corporation. A conventional retractor such as GELPI manufactured by George Tiemann Co., can be inserted through gap 25 to achieve lateral spreading of the tissue adjacent the vein. The light guide which is supported by support 28 illuminates the surgical site as the tissue is retracted as well as during dissection and litigation of the vein. After the branches of the vein are dissected within the reach of the instruments, the locking knob 16 is rotated counterclockwise to release the handle shaft 50 and allow the skin and subcutaneous tissue to return to its non-lifted (initial) position. The retractor 10 is then, in the same incision, reoriented 180° from the original position. The dissecting and ligating instruments can then be inserted again through gap 25 to separate the portion of the vein from the branches on the other side of the incision, i.e. to the right of the incision. As is apparent, this enables the portion of the vein to the right and the left of the incision to be dissected, limited by the reach of the instruments.

Figure 8:
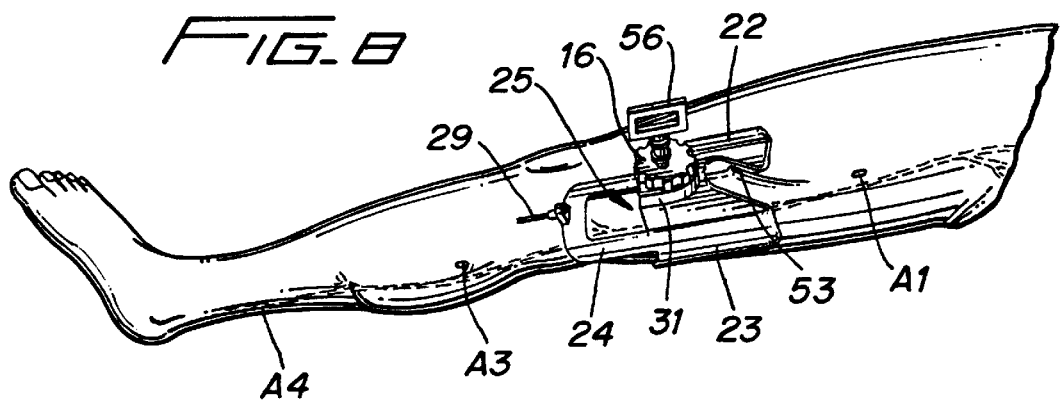
FIG. 8 is a perspective view similar to FIG. 7 illustrating the handle and retractor blade in the deployed position to separate the skin and subcutaneous tissue from the vein.

When the vein is severed in both directions through the first incision, the retractor 10 is then placed in the second incision A2. The skin and a portion of the subcutaneous tissue is lifted away from the vein as described above and the instruments are inserted to ligate and dissect the branches from the vein. Retractor 10 is then reoriented 180° in the incision A2 to ligate the portion of the vein extending in the other direction. FIG. 8 illustrates the retractor 10 positioned in the second incision oriented in the opposite direction from that shown in FIGS. 4–6. The retractor 10 is placed in each of the four incisions, oriented in both directions to access the vein in two directions. This enables access to the entire length of the vein through only four small incisions. Note that the extent the vein can be accessed in each direction through each incision is limited by the length of the ligating and dissecting instruments.

After all the branches are severed, the saphenous vein V is severed at both ends and removed from the leg through the incisions for use as a bypass graft. One way to remove the vein is to pull a portion of the vein up through incision A1, followed by pulling the vein portion around A1 through the incision A2, followed by A3 and finally through A4.

It should be appreciated that not only can more than four incisions be made, but fewer incisions can be utilized if a smaller section of the vein is desired or if longer instruments can be provided. Also, the order of insertion and orientation of the retractor 10 in each incision is not limited to the order discussed above.

The retractor 10 can be provided in a sterile package which includes the instrumentation for removing the vein from the leg. The kit, as shown by way of example in FIG. 9, includes a clip applied for ligating the branches of the vein, a dissector for severing the branches, and a grasper for holding the vein during dissection and ligation. An auto Suture* ENDO GRASP, ENDO SHEARS, and PREMIUM SURGICLIP* instrument are shown, designated by reference numerals 75, 85 and 95, respectively. Clearly, other combinations of instruments can be included in the kit. As illustrated, recesses conforming to the shape of the instruments are formed in tray 70 with accompanying shaped recesses formed in cover 72.

Note that the retractor 10 can be packaged fully assembled or packaged with three elements, i.e. the handle, base, and locking knob, separated for quick assembly by the user.

A second embodiment of the retractor is illustrated in FIGS. 10–13. Retractor 100 includes a base 112, a handle 114 and a locking knob 116. The base 112 functions in a similar manner as base 14, i.e., it rests on the patient's skin and mounts handle portion 114. However, as shown, it is different in configuration as, for example, extension 24 has been eliminated and walls 132 and 134 are angled at edges 135, 136 respectively.

The handle 114 has a hook portion or retractor blade 153 which progressively decreases in width towards the distal end to reduce the stress on the blade. A plurality of external threads 152 formed on shaft 150 engage the internal threads formed on locking knob 116. A pair of longitudinal grooves 151 (only one of which is shown) are formed along the length of the handle shaft 150 to create a projecting surface 154 which sits within the keyway (recess) 139 in the U-shaped inner wall 138 of neck portion 131 of base 112. This alignment of the projecting surface 154 and recess 139 ensure that the retractor blade 153 is oriented in the correct position during use and prevents rotation of handle portion 114.

On the portion of the handle shaft 150 opposite the projecting surface 154, (180° apart), is an elongated recess 158 configured to receive a light guide 170. As shown, the light guide 170 is in the form of a plastic tube which snaps into the elongated recess 158 and extends around the radiused portion 155 of retractor blade 153, terminating at distal tip 172 underneath retractor blade 153. The proximal end 174 of light guide 170 protrudes through opening 118 in handle grip 156 for connection to a conventional light source, such as Storz Coldlight Fountain. Thus, the light guide 170 provides means for enabling illumination for the surgical site. It should be appreciated that the means for enabling illumination can be positioned at other parts of the handle portion 114 or the base 112. For example, the tube 170 can be attached to the outside of the shaft 150. Also, although the means is disclosed as a light guide which cooperates with an independent light source, it is also contemplated that an illumination means which contains a light source can be included as part of the retractor.

The rotating knob 116 is similar to the rotating knob 16 of the first embodiment of FIGS. 1-3 except that instead of the flange 42, portion 139 of inner wall 138 extends upwardly to mount the locking knob 116. Locking knob 116 functions in an identical manner as locking knob 16 to retain the handle 114 and retractor blade 153 in the selected position.

The surgical retractor 100 is used in the identical fashion as retractor 10 described in FIGS. 4–8. The retractor 100 can also be packaged as a kit in the same manner as described above with respect to the first embodiment.

The retractor 10 or 100 can optionally be offered with retractor blades of different configurations. For example the retractor can be packaged as a kit including two or more handles having retractor blades of different sizes.

Figure 15:
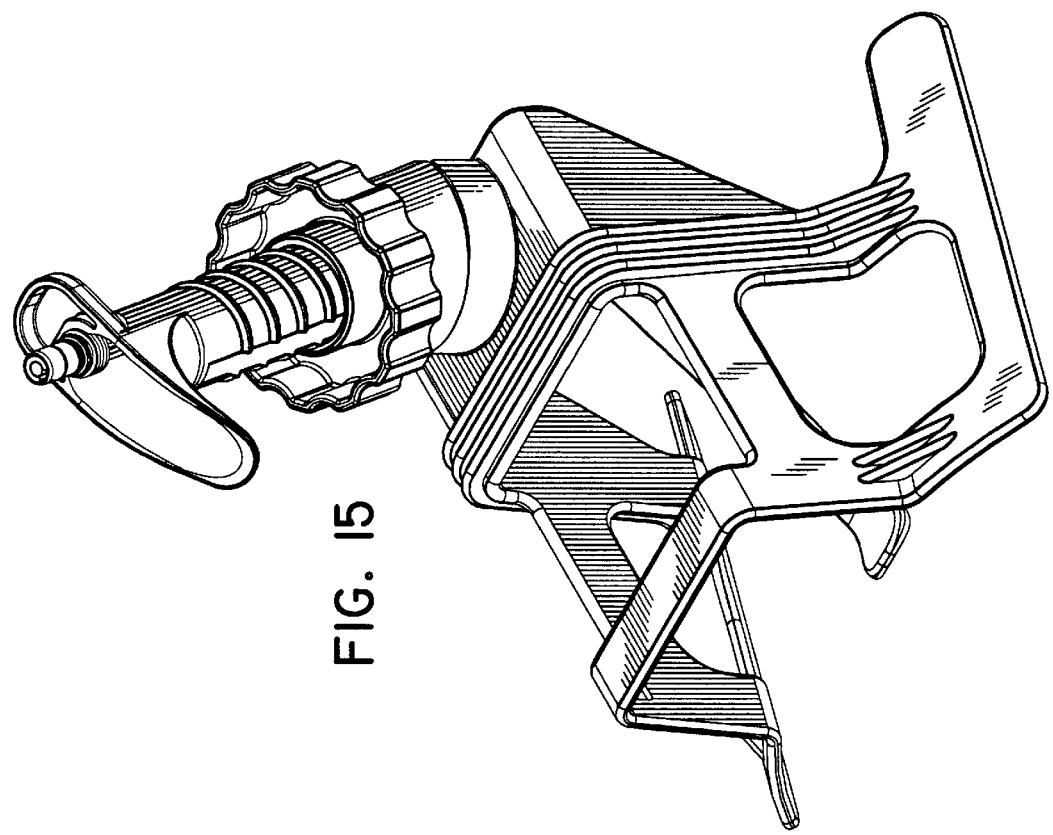
FIGS. 14 and 15 are front and rear perspective views of a third embodiment of the surgical retractor.
Figure 14:
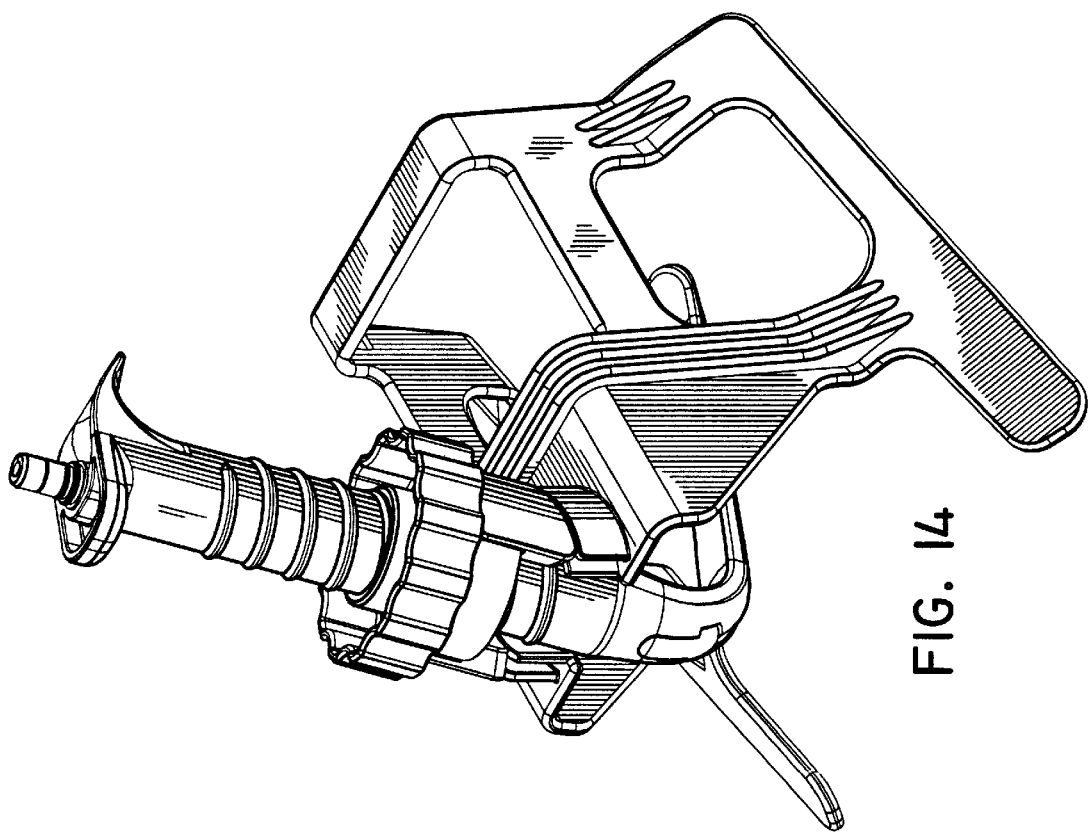
Figure 16:
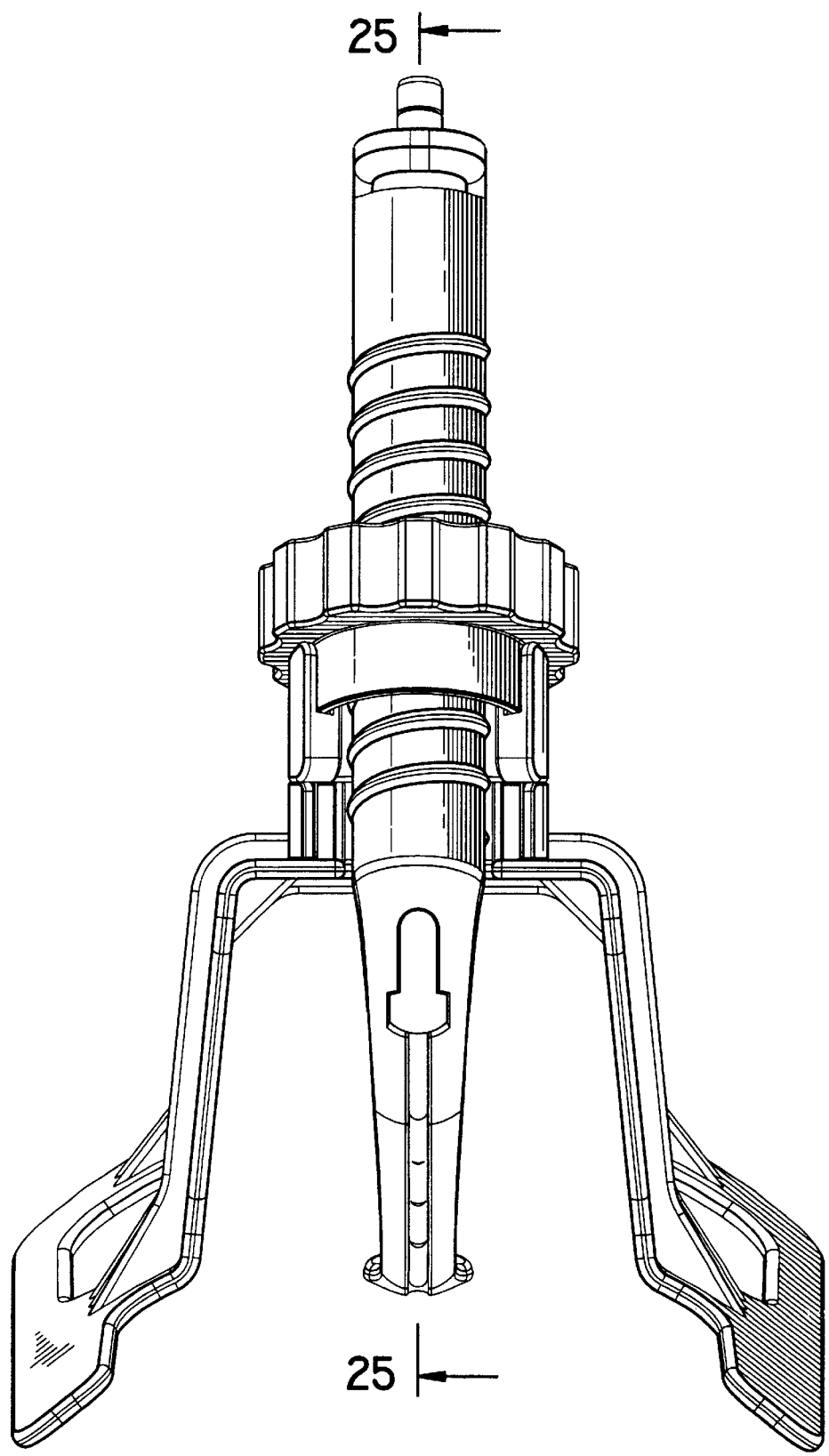
FIG. 16 is a front view of the retractor of FIG. 14.

A third embodiment of the retractor is illustrated in FIGS. 14–25. With reference first to FIGS. 14–16, retractor 200 includes a base 212, a handle 214 with retractor blade 253, an angle adapter 215 and a locking knob 216. The base 212 functions in a similar manner as base 112 of FIG. 10, i.e., it rests on the patient's skin and mounts shaft 250 of handle 214. However, as shown and described below, the base 212 differs in configuration from base 112.

Figure 25A:
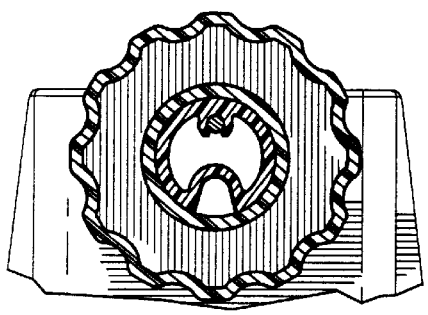
FIG. 25A is a cross sectional view taken along lines 25A—25A of FIG. 25.

As best shown in FIGS. 19–21, the hook portion or retractor blade 253 of handle 214 progressively decreases in width W towards the distal end to reduce the stress on the blade and has an upwardly angled flared tip 257 for increased is contact with the tissue. The retractor blade 253 is longer in length than blade 153 of FIG. 10 to enable retraction of more subcutaneous tissue. Flush holes 255 in the retractor blade 253 enable irrigation fluid to be injected through central channel 273 (FIGS. 25, 25A) for cleaning when the retractor is removed from the surgical site.

A plurality of external threads 252 formed on the outer surface of shaft 250 engage the internal threads formed on locking knob 216 in the manner described below. The handle 214 has an ergonomically designed tear drop shaped grip portion 260 which is preferably elongated in the direction of the retracting blade 253. An elongated groove 251 is formed along the length of the handle shaft 250 for mounting to base 212 as will be described in detail below.

Figure 25:
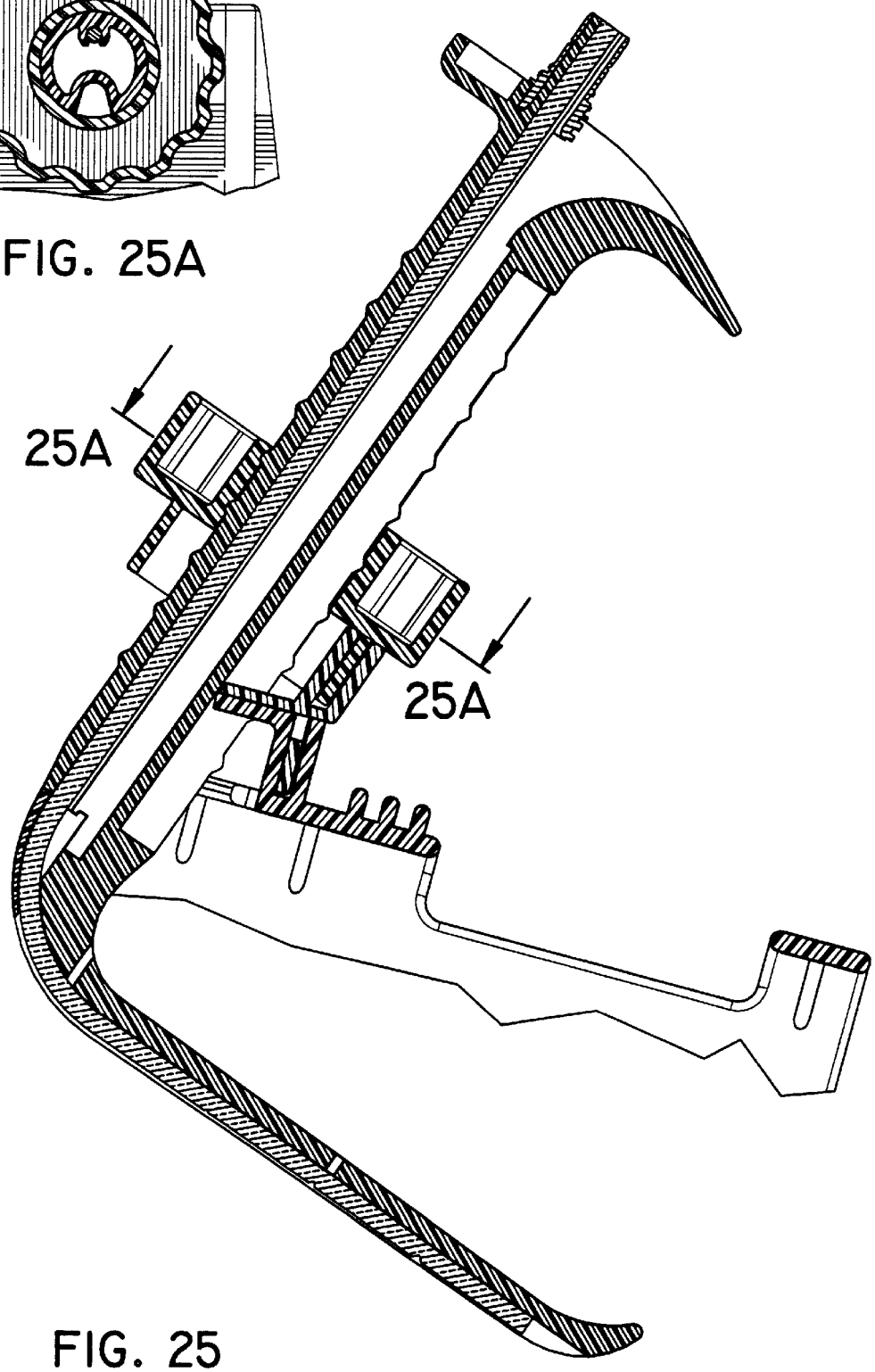
FIG. 25 is a cross sectional view of the retractor blade mounted on the base with the use of the angle adapter.

On the portion of the handle shaft 250 below the external threads 252 is a groove 258 for light guide 270 to provide means for enabling illumination of the surgical site. A light guide 270, illustratively in the form of an L-shaped plastic rod (see FIGS. 22 and 25) fits into the groove 258 such that the leg of the "L" extending around the radiused portion 269 of retractor blade 253 terminates proximally of flared tip 257. The other end of the "L" extends within central channel 273 (FIG. 25A) which is formed in hollow shaft 250 and terminates in post 283. A series of V-shaped facets 271, as shown in FIGS. 16 and 25, are formed in light guide 270 to increase the intensity of the light shining therethrough. A conventional light adapter 272 is mounted on post 283 to enable connection to a conventional light source, such as Storz Coldlight Foundation. Thus, the light shines through groove 258 of retractor blade 253 to illuminate the surgical site below the retractor blade 253. In a preferred embodiment, a light shield 280 (FIGS. 23 and 24) having flexible tabs 284 is snap fitted into recess 259 of shaft 250. The light shield 280 blocks a portion of the light which might otherwise shine towards the user. Note that light shield 280 includes a recess 289 to align with central channel 273 to receive the light guide 270.

It should be appreciated that although the means to illuminate the surgical site is disclosed as a light guide which cooperates with an independent light source, it is also contemplated that an illumination means which contains a light source can be included as part of the retractor.

Figure 22:
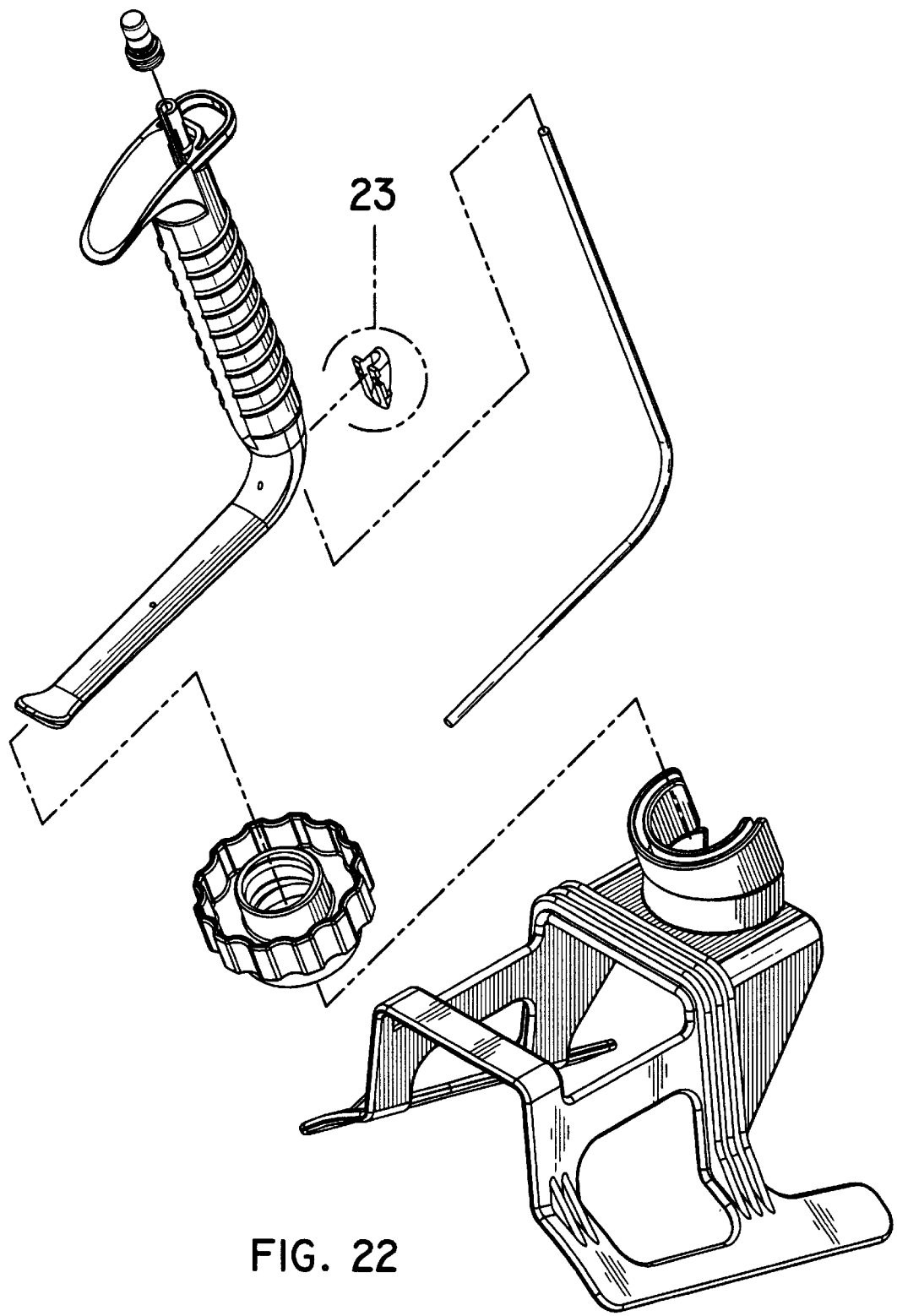
FIG. 22 is an exploded perspective view of the surgical retractor of FIG. 14.

The rotating (locking) knob 216, best shown in FIGS. 22 and 25, is similar to the locking knob 16 of the first embodiment of FIGS. 1–3. Knob 216 has a flange 219 and an annular wall 222 defining a circular opening 223 to threadingly receive shaft 250. Locking knob 216 functions in an identical manner as locking knob 16 to retain the handle 214 and retractor blade 253 in the selected position.

Figure 18:
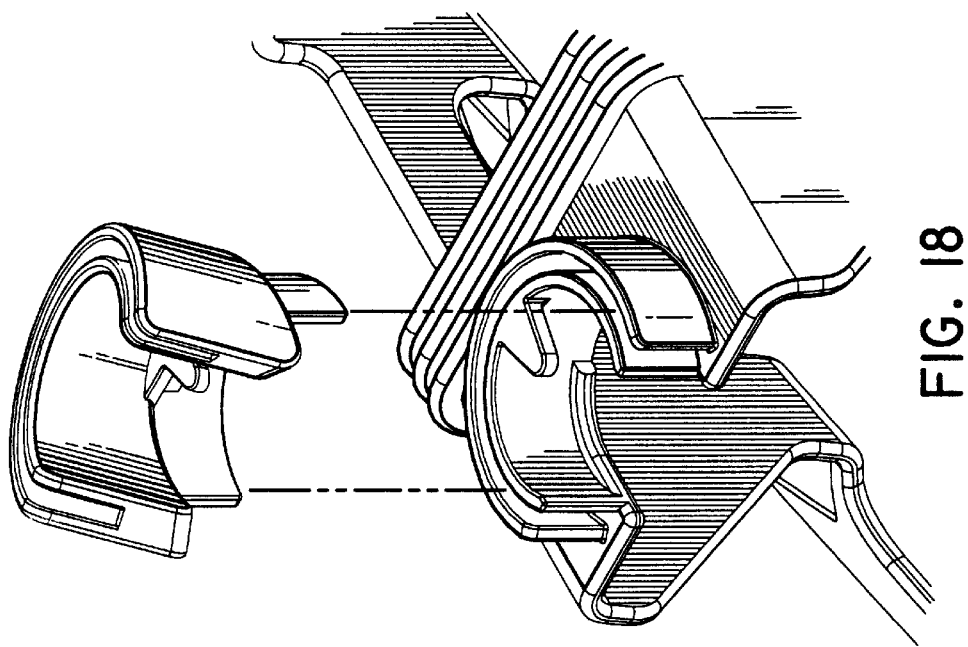
FIGS. 17 and 18 illustrate a side view and a top perspective view, respectively, of the angle adapter being mounted on the base.
Figure 17:
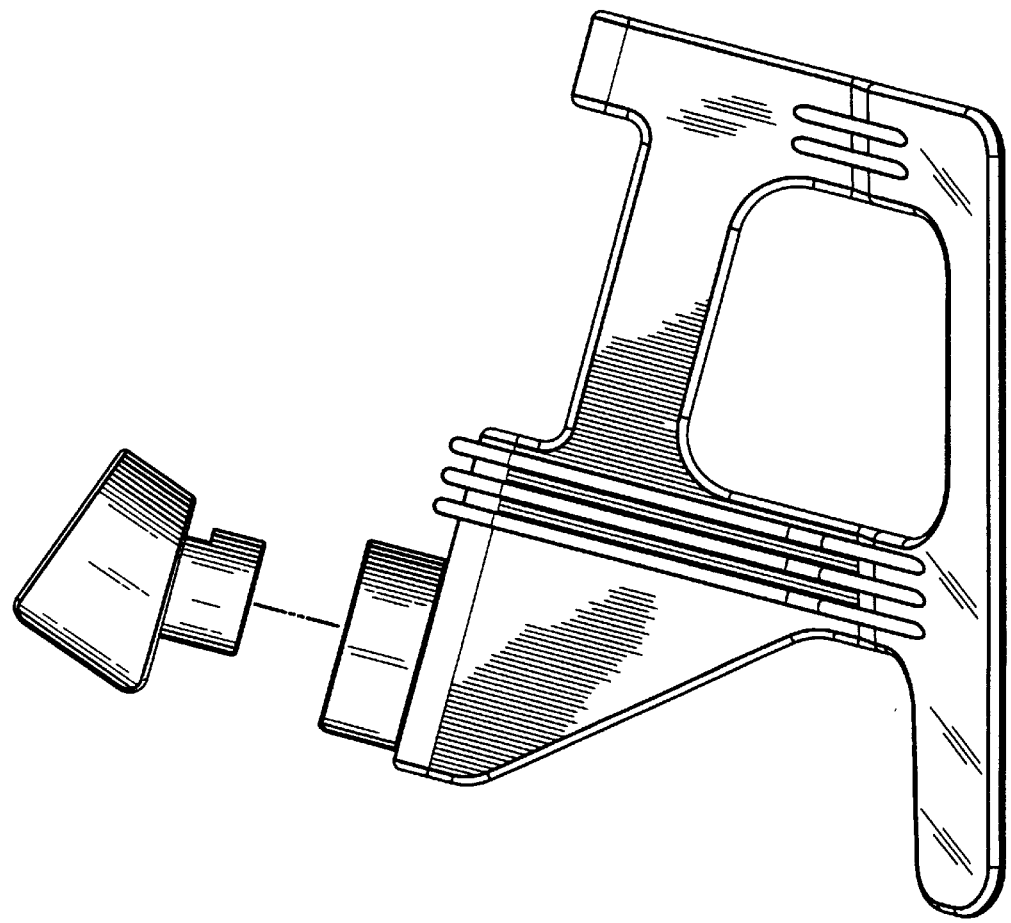

Turning now to base 212 and with reference to FIGS. 14–18B, base 212 includes a pair of spaced aparz legs 240 which are adapted to lie on the patient's skin. Legs 244 preferably lie at an angle A (FIG. 16) to the patient, which preferably ranges from about 40 to about 50 degrees and more preferably about 45 degrees. The upper surface of the base 212, which contains support or neck portion 231, is designated by reference numeral 232 and as shown in FIG. 18B, is angled from the front portion 234 to the rear (back) portion 236 so that the front portion lies above rear portion. This increases visibility of the surgical site during use and allows more space for insertion of the instrumentation for dissecting the vein as described above. This angling of the front portion also increases the angle of retractor blade 253 to increase its retracting function. Preferably the upper surface 232 lies at an angle C to a longitudinal axis L defined by a bottom edge of the legs 244. Angle C, preferably ranges from about 10 degrees to about 20 degrees, and more preferably about 15 degrees.

Side cutout portions 242 formed in base 212 help prevent collapsing of the tissue tunnel during use by reducing the amount of material at the legs which would otherwise press against the tissue. Cutouts 242 also enable excess tissue to extend therethrough, also to reduce collapsing of the tunnel. Side cutout portions 242 along with upper cutout portion 244 reduce the overall weight of retractor 200. A series of stabilizing ribs 238 are provided as shown to increase the stability of retractor 200.

With reference to FIG. 18, on the front portion 234 of upper portion 232, a pair of U-shaped walls, inner wall 233 and outer wall 235, are formed to receive either annular flange 219 of locking knob 216 or C-shaped flange 290 of angle adapter 215 described below. Projection 254 is configured to engage elongated groove 251 in shaft 250 for mounting the shaft 250 and preventing rotation thereof. Thus, the handle 214 with retractor blade 253 is mounted to base 212 for use in a similar manner as described above.

In certain applications, it may be desirable to increase the angle of the retracting blade 253 relative to the horizontal, i.e. the patient. This can be accomplished by mounting angle adapter 215 on neck portion 231. Flange 290 of angle adapter 215 extends between outer and inner walls 235, 233, of neck 231 and a pair of tabs 292 (only one is shown in FIG. 18) straddle projection 254 of neck portion 231 to prevent rotation of adapter 215. Projection 294 in recess 297 is configured to engage groove 251 of shaft 250. Flange 219 of locking knob 216 fits in groove 295 formed between U-shaped inner and outer walls 294, 296 of adapter 215 as the locking knob 216 functions in the identical manner as described above.

FIGS. 18A and 18B illustrate how the angle adapter 215 changes the angle of the retracting blade 253. In FIG. 18B, the handle 214 is mounted directly to the neck portion 231 without the use of an adapter. In this manner, by way of example, the retractor blade 253 forms an angle D of about 15 degrees with respect to longitudinal axis L. In FIG. 18A, when handle 214 is mounted to adapter 215, by way of example, the retractor blade 253 forms an angle E of about 35 degrees with respect to longitudinal axis L. Clearly other angles are contemplated in addition to those shown in FIGS. 18A and 18B.

Figure 27:
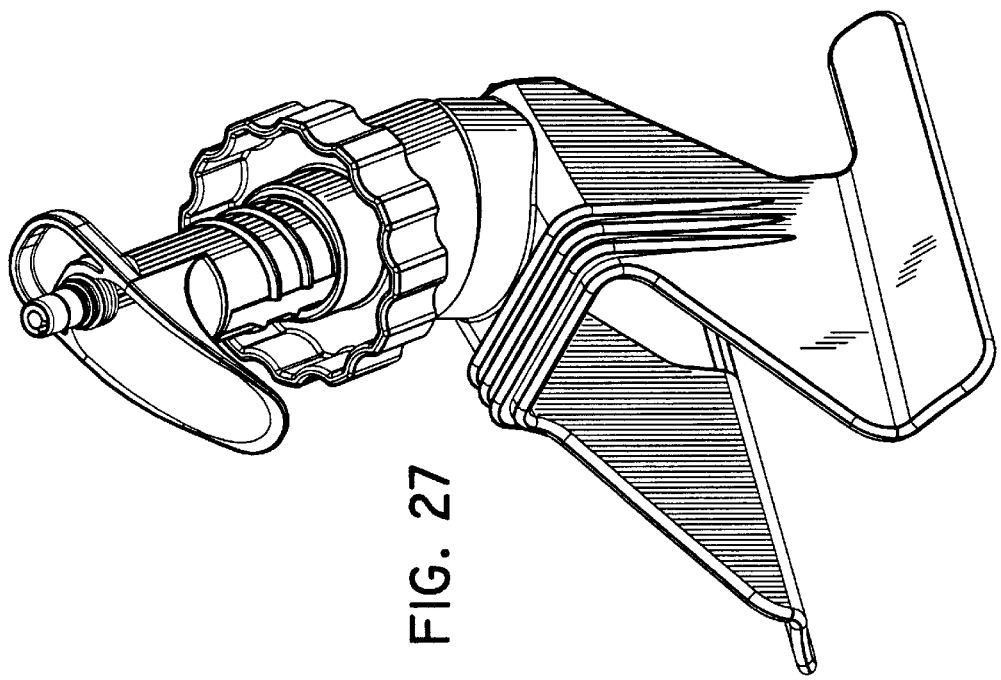
FIGS. 26 and 27 are front and rear perspective views of a fourth embodiment of the surgical retractor.
Figure 26:
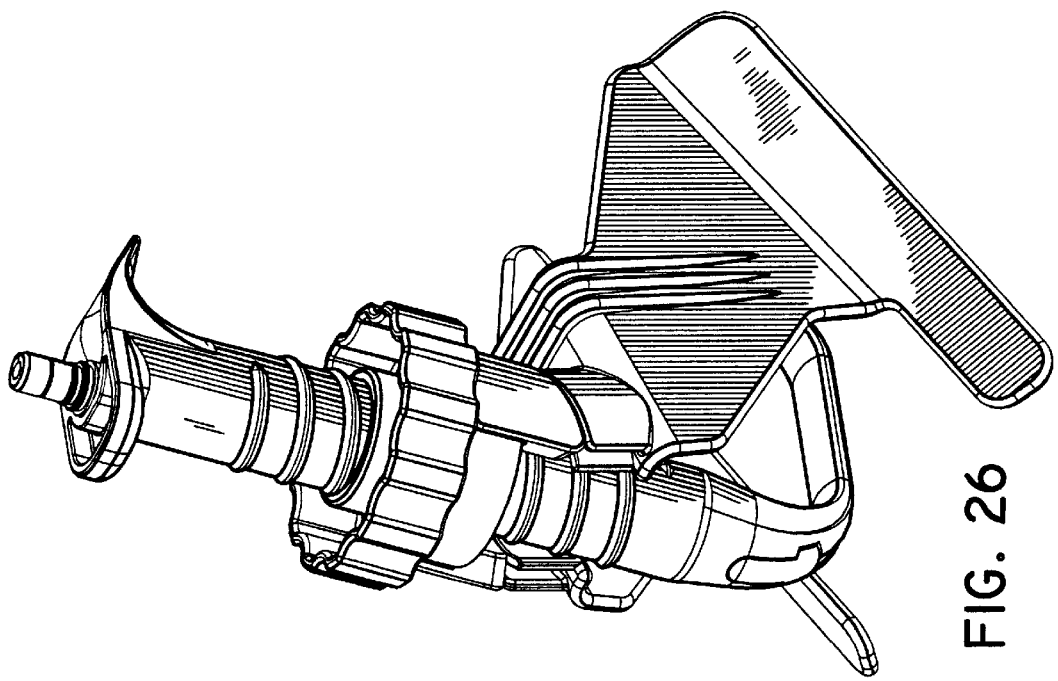

Another embodiment of the surgical retractor is illustrated in FIGS. 26 and 27 and designated by reference numeral 300. Retractor 300 is identical to retractor 200 except for the configuration of the base and the dimensions of the handle 314 and retracting blade 353 and its associated components. Although the base configuration differs, the walls of the neck portion of base 314 are the same size as that of neck portion 231 of base 212 so the same locking knob 216 and angle adapter 215 can be utilized.

Base 314 is a smaller more streamlined version. Legs 344 preferably lie at an angle to the patient of about 45 degrees (compare to angle A of FIG. 16), and the upper surface 310 preferably lies at an angle of about 15 degrees to the horizontal (compare to angle of C of FIG. 18B). Retractor 300 is used in an identical fashion to retractor 200.

Although described above for use in saphenous vein harvesting, the retractor can be used in other surgical procedures such as dissecting the internal mammary artery (IMA Harvest), in situ fem pops, appendectomies, vaginal hysterectomies.

It will be understood that various modifications may be made to the embodiments disclosed herein. For example, different shaped handles can be provided. Also the instrument can be entirely disposable or the entire instrument or parts thereof can be sterilized and reusable. Therefore, the above description should not be construed as limiting but as merely exemplifications of preferred embodiments. Those skilled in the art will envision other modifications within the scope and spirit of the claims appended thereto.

What is claimed is:

1. A surgical apparatus for retracting tissue comprising:
   a) a base adapted to lie on the patient's skin;
   b) an adapter removably mountable on the base;
   c) a retracting member mountable to the base at a first anile when the adapter is removed from the base and having a tissue engaging portion configured for insertion into the patient's body, the retracting member movable with respect to the base; and
   wherein when the adapter is mounted on the base, the retracting member mounted thereon is positioned at a second angle different from the first angle.

2. The apparatus of claim 1, further comprising a locking member securing the retracting member in position with respect to the base.

3. The apparatus of claim 2, further comprising a light guide mounted with respect to the retracting member to illuminate the surgical site.

4. The apparatus of claim 3, wherein the retracting member includes an elongated shaft and the locking member threadingly engages a portion of the elongated shaft.

5. The apparatus of claim 4, wherein the retracting member is integral with the elongated shaft.

6. The apparatus of claim 1, wherein the adapter has a recess to receive the shaft of the retracting member.

7. The apparatus of claim 6, wherein the adapter has a projecting surface configured to engage a groove in the shaft of the retracting member.

8. The apparatus of claim 1, wherein the retracting member terminates in a flared distal tip.

9. A surgical apparatus for retracting tissue comprising:
   a) a base;
   b) an elongated shaft movably mounted with respect to the base;
   c) a tissue retracting blade extending from the shaft and movable upon movement of the elongated shaft;
   d) a light guide mounted with respect to the elongated shaft for enabling illumination of the surgical site wherein a portion of the light guide is mounted within a channel in the shaft and a portion of the light guide is mounted in a recess formed in the tissue retracting blade; and
   e) a shield mounted with respect to the light guide to block a portion of the light emanating from the light guide.

10. A surgical apparatus for retracting tissue comprising:
   a) base;
   b) an elongated shaft movably mounted with respect to the base;
   c) a tissue retracting blade extending from the shaft and movable upon movement of the elongated shaft;
   d) a light guide mounted with respect to the elongated shaft for enabling illumination of the surgical site a portion of the light guide is mounted within a channel in the shaft; and
   e) a shield mounted with respect to the light guide to block a portion of the light emanating from the light guide wherein the shield is snap fitted into a recess in the shaft.

11. The surgical apparatus according to claim 9, wherein the retracting blade and elongated shaft are integral.

12. A surgical apparatus for retracting tissue comprising: a base and a tissue retracting member movably mounted with respect to the base, the retracting member having a tissue contacting portion configured for insertion into the patient's body, the tissue contacting portion having a curved portion extending away from the lower portion, the base having a front portion, a back portion, an upper portion and a lower portion adapted to lie on the patient and the retracting member being movable in a direction towards the upper portion and substantially transverse to the lower portion to lift body tissue, the upper portion having a support for receiving the retracting member, wherein the upper portion of the base is angled such that the front portion of the upper portion is raised with respect to the back portion of the upper portion.

13. A surgical apparatus according to claim 11, wherein the front portion of the upper portion is formed at an angle of about 10 to about 20 degrees with respect to a longitudinal axis defined by a lower edge of the base.

14. A surgical apparatus according to claim 12, further comprising an adapter removably mountable to the base to increase the angle of the tissue contacting portion with respect to the lower portion of the base.

15. A surgical apparatus according to claim 14, wherein the adapter includes a projecting surface configured to engage a groove formed in the retracting member.

16. A surgical apparatus according to claim 12, further comprising a light guide cooperating with the retracting member to illuminate the surgical site.

17. A surgical apparatus according to claim 12, wherein the retracting member includes a handle portion and a shaft portion intermediate the handle portion and the tissue contacting portion, and wherein the handle portion, shaft and tissue engaging portion being integral.

18. A surgical apparatus according to claim 17, further comprising a locking knob for retaining the retracting member in a selected position with respect to the base.

19. A surgical apparatus according to claim 18, wherein the locking member comprises a rotatable knob mounted on a shaft portion of the handle portion and the rotatable knob threadably engages threads on the shaft portion to retain the retracting blade in the selected position.

* * * * *